United States Patent
Arbabian et al.

(10) Patent No.: US 9,959,477 B2
(45) Date of Patent: May 1, 2018

(54) MAPPING OF BLOOD VESSELS FOR BIOMETRIC AUTHENTICATION

(71) Applicant: The Board of Trustees of the Leland Stanford Junior University, Palo Alto, CA (US)

(72) Inventors: Mohammad Amin Arbabian, San Francisco, CA (US); Seyed Miaad Seyed Aliroteh, Milpitas, CA (US); Hao Nan, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days. days.

(21) Appl. No.: 15/224,198

(22) Filed: Jul. 29, 2016

(65) Prior Publication Data

US 2016/0335514 A1    Nov. 17, 2016

Related U.S. Application Data

(63) Continuation-in-part of application No. 14/636,537, filed on Mar. 3, 2015, now abandoned.

(Continued)

(51) Int. Cl.
*G06K 9/00* (2006.01)
*G06K 9/20* (2006.01)
(Continued)

(52) U.S. Cl.
CPC ............ *G06K 9/209* (2013.01); *A61B 5/0093* (2013.01); *A61B 5/1171* (2016.02); *A61B 5/489* (2013.01);
(Continued)

(58) Field of Classification Search
CPC ... A61B 5/0095; A61B 5/0059; A61B 5/0093; A61B 5/05; A61B 5/0507; A61B 5/4312;
(Continued)

(56) References Cited

U.S. PATENT DOCUMENTS

| 4,255,971 A | * | 3/1981 | Rosencwaig | ...... G01N 21/1702 |
| | | | | 356/432 |
| 5,052,638 A | * | 10/1991 | Minovitch | ............. B64G 1/405 |
| | | | | 244/171.1 |

(Continued)

FOREIGN PATENT DOCUMENTS

CN    102269717    12/2012

*Primary Examiner* — Aklilu Woldemariam
(74) *Attorney, Agent, or Firm* — Lumen Patent Firm (57) ABSTRACT

Improved thermoacoustic imaging is provided by ensuring directional uniformity of the microwave excitation provided to the target being imaged. This directional uniformity can be quantified in terms of the eccentricity e of the polarization ellipse of the microwave excitation. We have $e \leq 0.87$, preferably $e \leq 0.71$, and more preferably $e \leq 0.32$. Optical excitation can be provided in addition to the microwave excitation. Excitation can be performed at multiple optical wavelengths and/or microwave frequencies to improve depth uniformity. In addition, the employment of excitation cells with optimized spacing and geometry provides the uniformity in another two degrees of freedom. One potential application is to detect blood vessel in user's finger for biometric authentication.

29 Claims, 7 Drawing Sheets

Related U.S. Application Data (60) Provisional application No. 61/947,241, filed on Mar. 3, 2014, provisional application No. 62/127,101, filed on Mar. 2, 2015.

(51) Int. Cl.
*A61B 5/00* (2006.01)
*A61B 5/1171* (2016.01)

(52) U.S. Cl.
CPC ....... *G06K 9/00885* (2013.01); *G06K 9/2018* (2013.01); *G06K 9/00* (2013.01); *G06K 2009/00932* (2013.01)

(58) Field of Classification Search
CPC ....... A61B 5/412; A61B 6/037; A61B 5/0073; A61B 5/053; A61B 5/7228; A61B 8/4272; A61B 5/1171; A61B 5/489; G01N 21/17; G01N 21/1702; G01N 2291/02863; G01N 29/2418; G01N 2223/405; G01N 2223/508; G01N 33/492; G06K 9/00; G06K 9/00382; G06K 9/00228; G06K 9/00597; G06K 2009/00932; G06K 9/00885; G06K 9/209; G06K 9/2018; G07C 9/00158; B01L 2300/168; B60K 28/066; C12Q 1/6809; G06F 19/703; G06F 19/321; G06F 3/04812; G06F 3/04842; G06T 2207/30168; G06T 7/0012; G06T 7/11; H04N 5/23222; H04N 13/02; H04N 5/2254; H04N 5/2253; H04N 5/2258; G01R 29/0878; Y10S 378/901; H01L 27/14621; H01L 27/14645; H01L 2924/0002; H01L 31/02325; H01L 27/14627; H01L 2924/00; H01L 27/14618; H01L 27/14625; H01L 27/14634; H01L 31/0232
USPC ................ 382/115, 124, 128; 600/431, 407; 348/340, 290, 291, 335, 342, 360, 363
See application file for complete search history.

(56) References Cited

U.S. PATENT DOCUMENTS

| | | | |
|---|---|---|---|
| 6,006,175 A * | 12/1999 | Holzrichter | A61B 5/0507 704/205 |
| 6,078,253 A * | 6/2000 | Fowler | G06K 9/00335 307/116 |
| 6,182,499 B1 * | 2/2001 | McFarland | B01J 19/0046 422/68.1 |
| 6,212,421 B1 * | 4/2001 | Vo-Dinh | A61B 5/0091 600/407 |
| 6,216,025 B1 * | 4/2001 | Kruger | A61B 5/0095 128/915 |
| 6,898,299 B1 | 5/2005 | Brooks | |
| 7,266,407 B2 | 9/2007 | Li et al. | |
| 7,728,902 B2 | 6/2010 | Kishigami et al. | |
| 7,990,336 B2 * | 8/2011 | Maines | H01J 25/00 343/742 |
| 8,229,179 B2 | 7/2012 | Sato | |
| 8,811,689 B2 | 8/2014 | Kiyomizu et al. | |
| 2004/0052328 A1 * | 3/2004 | Sabol | G06T 7/0012 378/37 |
| 2006/0028962 A1 * | 2/2006 | Zachar | G11B 7/005 369/112.01 |
| 2007/0064572 A1 * | 3/2007 | Zachar | G11B 7/131 369/110.01 |
| 2008/0114274 A1 * | 5/2008 | Moonen | A61N 7/02 601/3 |
| 2010/0187224 A1 * | 7/2010 | Hyde | H05B 6/705 219/720 |
| 2010/0328033 A1 | 12/2010 | Kamei et al. | |
| 2011/0040176 A1 | 2/2011 | Razansky et al. | |
| 2011/0306857 A1 | 12/2011 | Razansky et al. | |
| 2012/0123256 A1 | 5/2012 | Razansky et al. | |
| 2012/0309636 A1 * | 12/2012 | Gibbons | B01L 3/0275 506/9 |
| 2013/0184555 A1 * | 7/2013 | Chen | A61B 5/0088 600/407 |
| 2015/0020034 A1 * | 1/2015 | Okuley | G06F 1/1616 715/863 |
| 2015/0316511 A1 * | 11/2015 | Guo | H04B 10/27 398/140 |

* cited by examiner

MAPPING OF BLOOD VESSELS FOR BIOMETRIC AUTHENTICATION

CROSS REFERENCE TO RELATED APPLICATIONS

This application is a continuation in part of U.S. Pat. No. 14/636,537, filed on Mar. 3, 2015, and hereby incorporated by reference in its entirety.

Application Ser. No. 14/636,537 claims the benefit of U.S. provisional patent application 61/947,241, filed on Mar. 3, 2014, and hereby incorporated by reference in its entirety.

Application Ser. No. 14/636,537 claims the benefit of U.S. provisional patent application 62/127,101, filed on Mar. 2, 2015, and hereby incorporated by reference in its entirety.

FIELD OF THE INVENTION

This invention relates to thermoacoustic imaging.

BACKGROUND

Thermoacoustic imaging involves illuminating a target with microwaves and performing acoustic imaging of sound generated in the target by the thermoacoustic effect. Photoacoustic imaging is a similar physical effect using an optical excitation as opposed to a microwave excitation.

Although these effects have been used in imaging for some time now, it remains desirable to improve their performance to enable new and challenging applications. Accordingly, it would be an advance in the art to provide improved thermoacoustic imaging.

SUMMARY

One potential application for thermacoustic imaging is biometric authentication based on the pattern of blood vessels in a user's finger. This is a challenging application for thermoacoustic imaging, since the relevant size scale is much less than in conventional applications such as whole-body or organ-scale imaging.

Figure 5A:
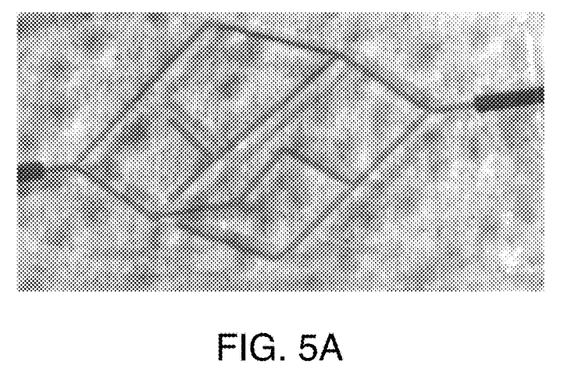
FIG. 5A is an image of a phantom that simulates blood vessels in tissue.
Figure 5B:
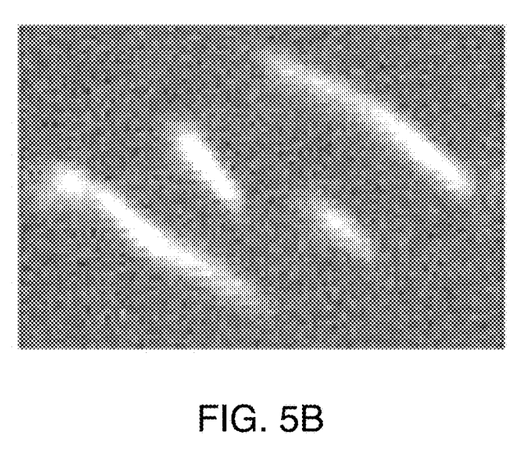
FIG. 5B is a thermoacoustic image of the phantom of FIG. 5A making use of linearly polarized microwaves from 2-element emitters.
Figure 5C:
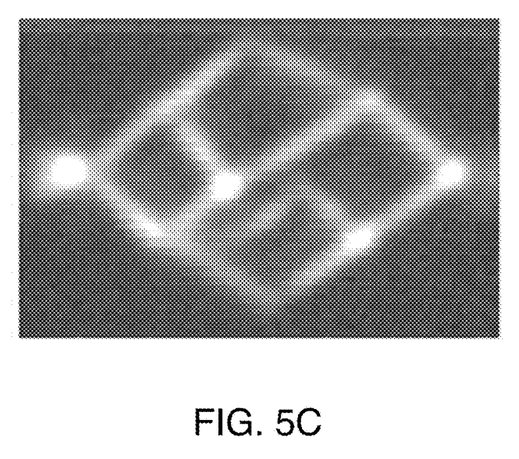
FIG. 5C is a thermoacoustic image of the phantom of FIG. 5A making use of circularly polarized microwaves from 4-element emitters, in accordance with principles of the present invention.

In addition to various challenges related to this change of scale, we have unexpectedly found that the polarization of the microwave excitation is critical for getting good thermoacoustic images of vessel-like structures. FIG. 5B is a thermoacoustic image of the phantom of FIG. 5A, and illustrates this problem. Structures in the phantom that are unfavorably aligned with the linear microwave polarization used for this image are not seen in the image, which is a catastrophic lack of image quality. FIG. 5C shows a corresponding thermoacoustic image of the phantom of FIG. 5A according to principles of the invention. Linear polarization of the microwaves is avoided, and the resulting image is much more accurate than the image of FIG. 5B. Polarization can be quantified by referring to the eccentricity e of the polarization ellipse. Embodiments of the invention have e≤0.87. Preferred embodiments have e≤0.71. Particularly preferred embodiments have e≤0.32.

In some embodiments, optical excitation is combined with microwave excitation. It is convenient to regard these embodiments as also relating to thermoacoustic imaging, so we define thermoacoustic imaging as acoustic imaging based on microwave or microwave+optical excitation.

DETAILED DESCRIPTION

Figure 1:
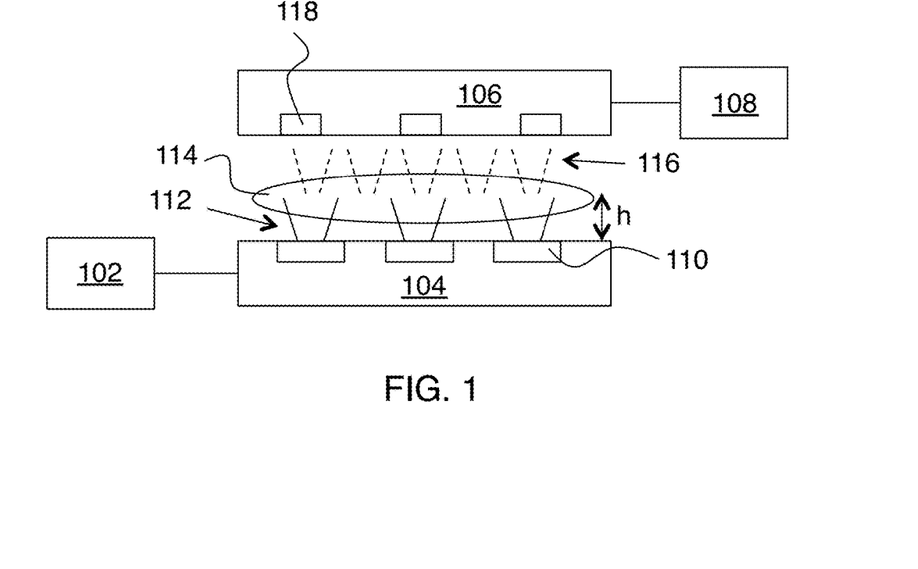
FIG. 1 shows a first embodiment of the invention.

FIG. 1 shows a first embodiment of the invention. In this example, a microwave source 102 is configured to provide a microwave output. A microwave emitter array 104 includes two or more unit cells 110, which can be identical or dissimilar. As described in greater detail below, the unit cells each include three or more near-field excitation elements. Microwave emitter array 104 is configured to receive the microwave output from microwave source 102, and to provide microwave excitation 112 to a target 114 via the near-field excitation elements of the unit cells 110. The spacing between the microwave emitter and a typical position within the target is referenced as h. We define "near-field" to be within 10 wavelengths of the emitter within the target. For example, at 9 GHz the near-field region is within about 3 mm of the emitter in tissue.

An acoustic sensor array 106 includes one or more sensor elements 118 that are configured to receive acoustic signals 116 from target 114 responsive to microwave excitation 112. A processor 108 is configured to receive signals from acoustic sensor array 106 and to provide an acoustic image of target 114. The microwave emitter array can be periodic or aperiodic. As described in greater detail below, the microwave emitter array can be integrated with other sensors and/or excitation sources, such as optical excitation sources and/or acoustic sensors.

In this example, the acoustic sensor array and the microwave emitter array are disposed on opposite sides of the target. It is also possible for the acoustic sensor array and the microwave emitter array to be disposed on the same side of the target, e.g. as in the example of FIG. 6 below.

Various possibilities exist for the microwave source. Preferred pulsed embodiments provide microwave pulses having a duration of 1 µs or less, a peak power of 0.1 W or more, and a repetition rate of 1 Hz or more. Alternatively, the microwave source can be configured to provide a continuous amplitude-modulated microwave output, such as Frequency-Modulated Continuous Wave (FMCW) or Stepped-Frequency Continuous Wave (SFCW). The frequency (or frequencies for multi-frequency excitation) is preferably between 0.1 GHz and 20 GHz.

In preferred embodiments, crosstalk is mitigated using various strategies. For example non-adjacent unit cells of the microwave emitter array can be activated in sequence in order to reduce cross-talk between different unit cells. Another mitigation strategy is to activate non-adjacent sensor elements of the acoustic sensor array in sequence in order to reduce cross-talk between different sensor elements. This pattern of activation can be a simple interleaved pattern or a pseudo-random activation of elements.

The sensor array elements can be individually tuned to different acoustic frequencies. These acoustic frequencies are preferably in a range from 1 MHz to 30 MHz to provide high sensitivity and high resolution simultaneously.

Figure 2:
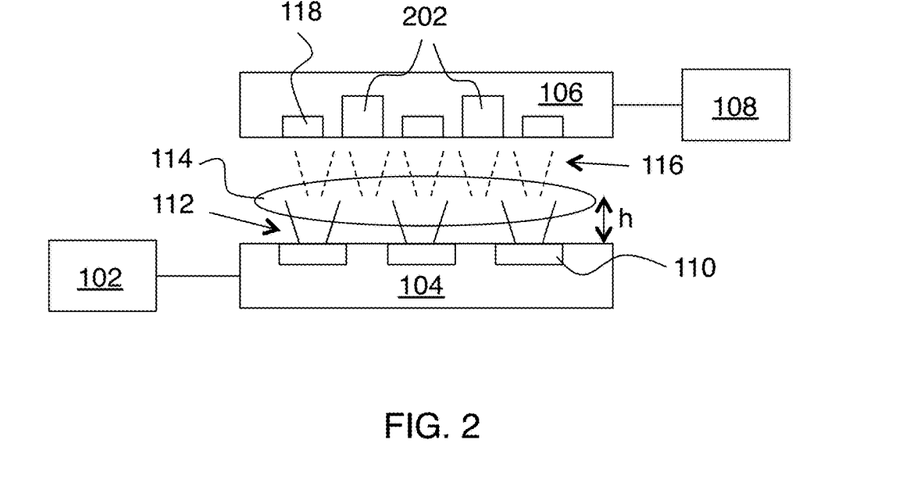
FIG. 2 shows a second embodiment of the invention.

FIG. 2 shows a second embodiment of the invention. This embodiment is similar to the embodiment of FIG. 1, except that one or more auxiliary sensors 202 are added. Such sensors can be microwave sensors, optical sensors or acoustic sensors. Various functions can be provided by such auxiliary sensors, including but not limited to: 1) monitoring and calibrating the microwave excitation, 2) monitoring and calibrating the optical radiation, 3) obtaining course-grain information about the target geometry and its motion, 4) providing signals for cancellation of microwave to acoustic leakage directly with analog electronics, 5) providing signals for cancellation of microwave to acoustic leakage computationally in post-processing, 6) providing signals for cancellation of optical to acoustic leakage directly with analog electronics, and 7) providing signals for cancellation of optical to acoustic leakage computationally in post-processing.

Functions 2, 6 and 7 in this list relate to below-described embodiments that include optical excitation of the target in addition to microwave excitation of the target.

Figure 3:
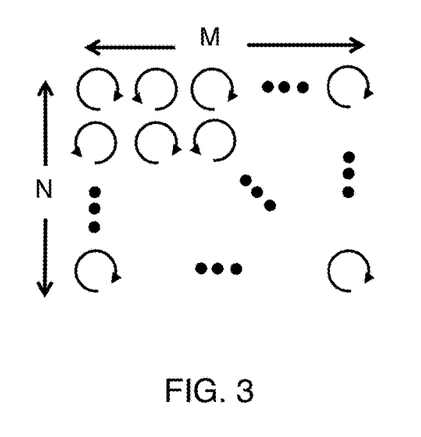
FIG. 3 shows a preferred microwave excitation array for use in embodiments of the invention.

As indicated above, it is important to avoid the use of a linearly polarized microwave excitation. Circular polarization is most preferred, although some deviation from circular polarization is permissible. FIG. 3 schematically shows a preferred microwave excitation array for use in embodiments of the invention. Here each element emits with circular polarization (as shown), and there is also an alternating pattern of clockwise and counterclockwise rotation in the polarizations. The alternating pattern of clockwise and counterclockwise rotation in the polarization is a consequence of the sharing of excitation elements between adjacent excitation cells, to create a more economical design. However, this is not a strict requirement for proper device operation and thus it is possible to employ a single clockwise or counterclockwise polarization in all excitation cells by not sharing any excitation elements between cells. In general, such an emitter array can have N rows and M columns, although either M or N can be 1 to provide a 1-D array.

Figure 4A:
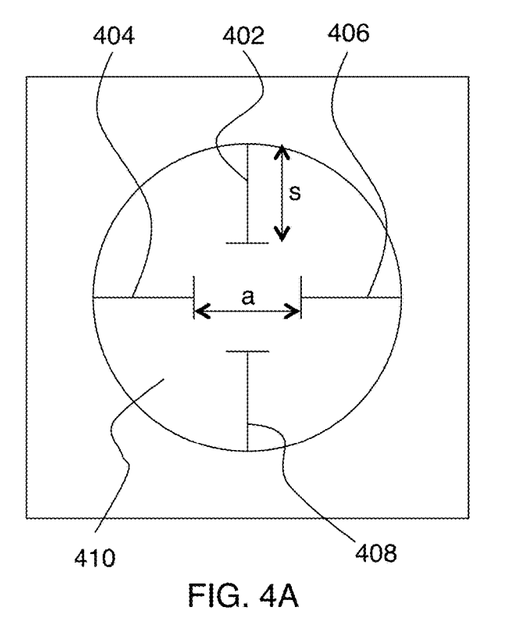
FIG. 4A shows an exemplary unit cell of the microwave excitation array that includes several near-field excitation elements.

FIG. 4A shows an exemplary unit cell of the microwave excitation array that includes several near-field excitation elements. In this example, four T-shaped near field excitation elements (402, 404, 406, and 408) are disposed in an aperture 410. We can create a directionally uniform excitation by generating a rotating electric field using three or more near field excitation elements fed with RF phases that are equally spaced in the 0 to 360 degree range. In this example, 4 near field excitation elements are shown that are fed with 0, 90, 180, and 270 degree phases. The geometrical parameters a and s on FIG. 4A are preferably related to other design parameters as follows: $a \approx \sqrt{2}h$, $a \approx \lambda/2$, $s \approx a$. Microwave frequency f and wavelength $\lambda$ are related by $f\lambda = c/\sqrt{\epsilon}$, where $\epsilon$ is the effective dielectric constant of the target material at frequency f, and c is the speed of light.

Figure 4B:
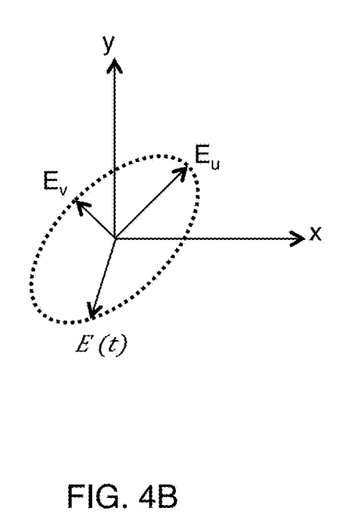
FIG. 4B shows notation for describing elliptical polarization.

Here it is helpful to consider the polarization of the microwaves in more detail. FIG. 4B shows notation for describing elliptical polarization. In general, the time evolution of the electric field of an electromagnetic excitation in a reference plane describes an ellipse, which we refer to as the polarization ellipse. Let $E_u$ be the electric field magnitude of the major axis of the polarization ellipse (as shown). Let $E_v$ be the electric field magnitude of the minor axis of the polarization ellipse (as shown). The eccentricity e of the polarization ellipse is defined by $$e = \sqrt{1 - \left(\frac{E_v}{E_u}\right)^2}.$$

We define directional uniformity of the thermoacoustic signal as follows. Let $TA_+$ be the thermoacoustic signal obtained from a linear target (such as a blood vessel) that is aligned with $E_u$. Let $TA_-$ be the thermoacoustic signal obtained from a linear target that is aligned with $E_v$. Then the directional uniformity U is given by $$U = \frac{TA_+ - TA_-}{TA_+}.$$

We have $U \leq 0.75$, more preferably $U \leq 0.5$ and most preferably $U \leq 0.1$. Since $$\frac{TA_-}{TA_+} = \left(\frac{E_v}{E_u}\right)^2$$

we have $e = \sqrt{u}$, so we see that $e \leq 0.87$, more preferably $e \leq 0.71$, and most preferably $e \leq 0.32$. Relative phases of excitation elements of the unit cells of the emitter array are preferably selected to provide sufficiently low eccentricity in a reference plane within the target and parallel to the emitter array. It is convenient to refer to this arrangement of the reference plane as being "within the target".

The significance of providing directional uniformity as described above is clearly shown on FIGS. 5A-C. Here FIG. 5A is an image of a phantom that simulates blood vessels in tissue. It includes long thin structures at various directions as can be expected of blood vessels in tissue. FIG. 5B is a thermoacoustic image of the phantom of FIG. 5A making use of linearly polarized microwaves from 2-element emitters. Here it is apparent that the image is seriously distorted. Investigation has confirmed that these poor imaging results are a result of unfavorable alignment between features being imaged and the linear polarization of the microwave excitation.

FIG. 5C is a thermoacoustic image of the phantom of FIG. 5A making use of circularly polarized microwaves from 4-element emitters, in accordance with principles of the present invention. Here it is seen that much better imaging results are obtained.

Figure 6:
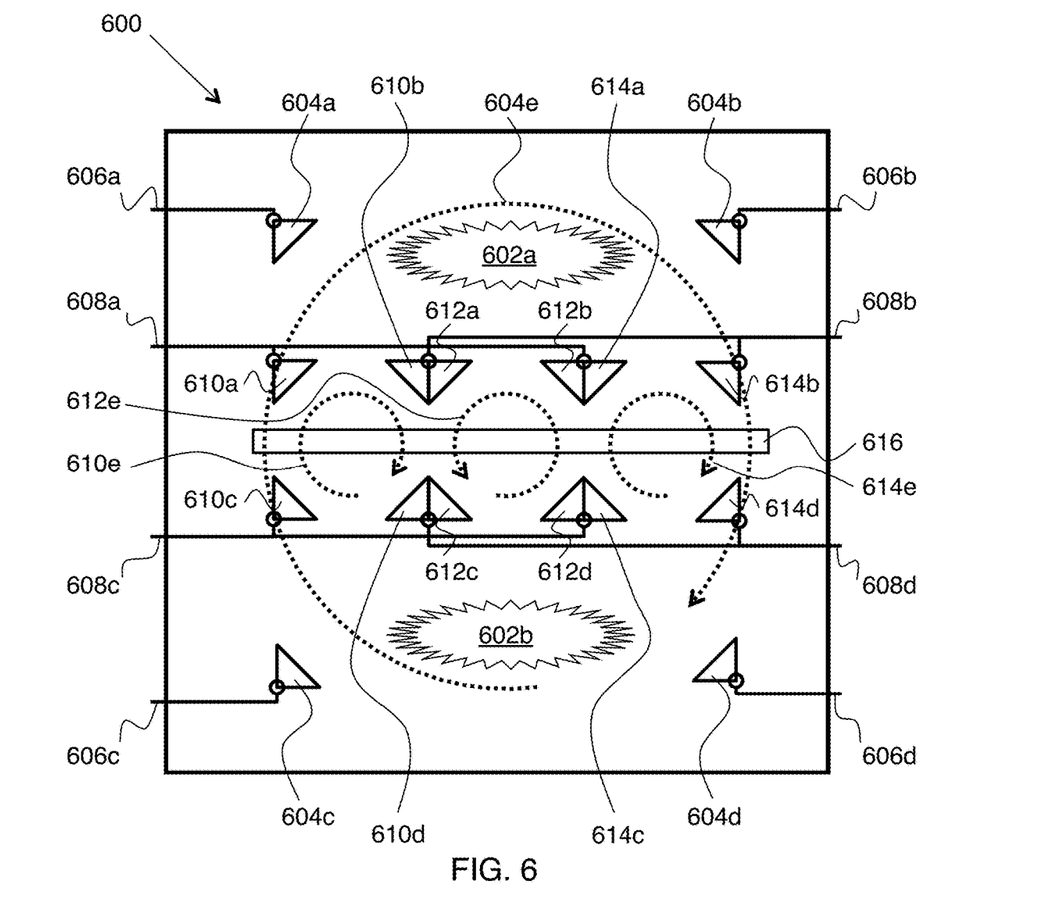
FIG. 6 shows an exemplary excitation and sensor array featuring integration of optical sources, microwave excitation and an acoustic sensor array.

Some embodiments of the invention further include providing optical radiation to the target to improve thermoacoustic imaging. The main idea is to make the overall energy deposition provided by the system more uniform by appropriately combining microwave excitation and optical radiation. In such embodiments, it is preferred to integrate optical sources, microwave emitters and the acoustic sensor array on the same surface. FIG. 6 shows an example of this approach.

Here 600 is the integrated device, shown in a view looking down on the device from where the target would be in operation. Here 602a and 602b are optical sources configured to provide optical radiation to the target, and in this design are intended to provide 0 to 2 mm penetration depth in tissue. Preferred optical wavelength(s) for this excitation are between 750 nm and 1500 nm. Microwave emitters 604a, 604b, 604c, and 604d provide an outer microwave excitation 604e, intended to provide excitation from 5 mm to 15 mm depth in tissue. Inputs 606a, 606b, 606c, 606d to emitters 604a, 604b, 604c, 604d have equally spaced relative phases as described above to provide sufficient directional uniformity.

The 2 mm to 5 mm depth range in tissue is covered by an array of three unit cells. Inner microwave excitation 610e is provided by emitters 610a, 610b, 610c, 610d. Inner microwave excitation 612e is provided by emitters 612a, 612b, 612c, 612d. Inner microwave excitation 614e is provided by emitters 614a, 614b, 614c, 614d. These emitters are driven by inputs 608a, 608b, 608c, 608d having equally spaced phases as described above to provide sufficient directional uniformity. The pattern of connections between inputs 608a, 608b, 608c, 608d and the emitters for the array lead to opposite polarization rotation for excitation 612e compared to excitations 610e and 614e.

Here 616 is the acoustic sensor array. In this example, the acoustic sensor array and the microwave emitter array are disposed on the same side of the target.

The microwave excitation and the optical radiation can be provided to the target synchronously using a single trigger signal. Alternatively, the microwave excitation and the optical radiation can be provided sequentially in alternation.

This is an example of combining one large, low-frequency microwave excitation cell with several smaller high-frequency microwave excitation cells and optical cells to create a more uniform excitation along the depth. Uniform field distribution in depth is improved by using a combination of optical excitation together with multiple-frequency microwave excitation. Optical excitation is optimized in the closest region, high frequency microwave is optimized in the mid region, and low frequency microwave is optimized in the far region. A combination of frequency selection together with selection of the excitation cell geometries and locations can provide a uniform excitation. The spacing and geometry of the excitation cells can be optimized for different frequencies.

Figure 7:
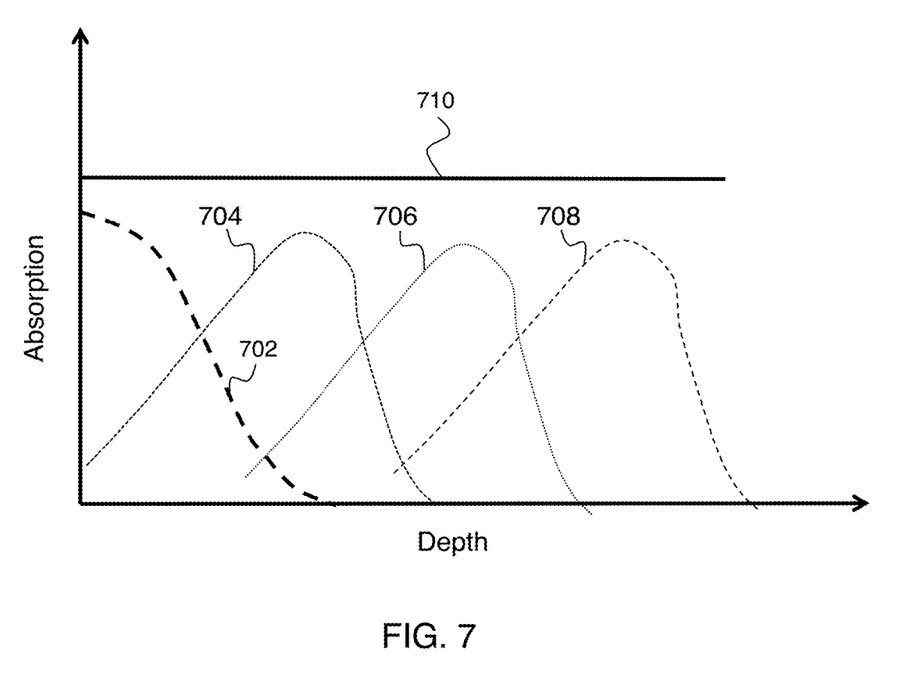
FIG. 7 schematically shows how improved depth uniformity can be provided by using optical excitation and microwave excitation at several different microwave frequencies.

FIG. 7 schematically shows how improved depth uniformity can be provided by using optical excitation and microwave excitation at two or more different microwave frequencies. Here 702 is the optical excitation, 704 is microwave excitation at a first RF frequency $f_1$, 706 is microwave excitation at a second RF frequency $f_2$, and 708 is microwave excitation at a third RF frequency $f_3$. Microwaves at lower frequencies have greater penetration depth in tissue, so we have $f_1 > f_2 > f_3$ for biometric applications. The overall energy deposition is schematically shown as 710, and is significantly more uniform than the deposition from any one of the sources. Thus the microwave signals at the two or more frequencies are configured to enhance depth uniformity of thermoacoustic imaging.

Depth uniformity is defined with respect to energy deposition in a homogeneous target. A deposition pattern is considered to have depth uniformity if the energy deposition at a depth of minimum energy absorption within a predetermined depth range is 25% or more of the energy deposition at a depth of maximum energy absorption within the predetermined depth range. For example, this predetermined depth range can be 0-10 wavelengths of the microwave excitation being used.

In the example of FIG. 7, the target has a first region closer to a surface of the target than a second region, and the optical radiation is mainly provided to the first region, while the microwave excitation is mainly provided to the second region.

Although the example of FIG. 7 shows use of only a single optical wavelength, two or more optical wavelengths can be employed to improve depth uniformity. In such cases, the optical source can be configured to provide optical radiation at two or more optical wavelengths, and the optical radiation at the two or more optical wavelengths can be configured to enhance depth uniformity of thermoacoustic imaging.

Figure 8:
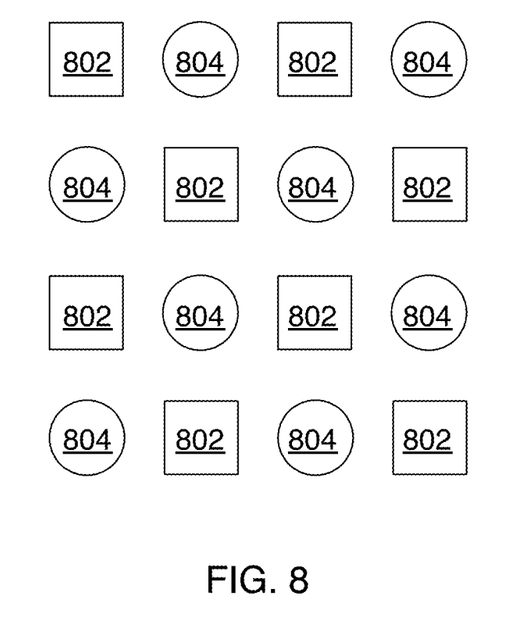
FIG. 8 shows a first exemplary alternating arrangement of optical sources and microwave emitter array unit cells.
Figure 9:
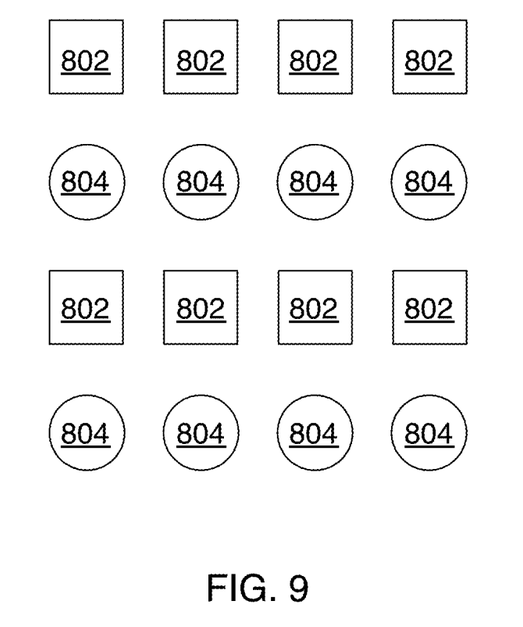
FIG. 9 shows a second exemplary alternating arrangement of optical sources and microwave emitter array unit cells.

Optical emitters and the unit cells of the microwave emitter array can alternate. FIG. 8 shows a checkerboard pattern of alternating microwave unit cells 802 and optical emitters 804. FIG. 9 shows row by row alternation of microwave unit cells 802 and optical emitters 804.

Figure 10:
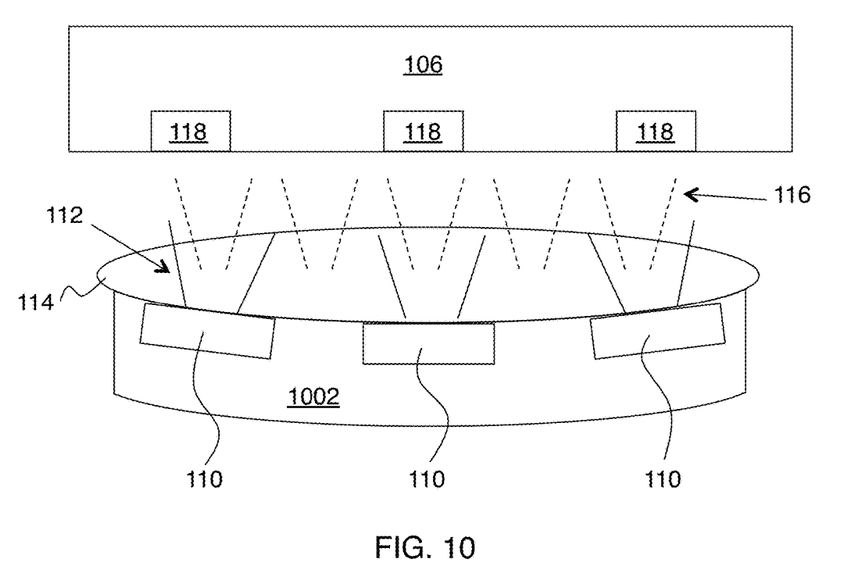
FIG. 10 shows an embodiment of the invention that is flexible in order to conform to the shape of the target being imaged.

Practice of the invention does not depend critically on the overall mechanical configuration. In some cases, the apparatus is rigid and planar. In other cases, the apparatus is flexible in order to conform to a shape of the target. FIG. 10 shows an example along these lines. Here microwave emitter array 1002 is flexible and can conform to the shape of target 114 in operation. The apparatus can also be rigid and have a non-planar geometry, such as cylindrical and hemispherical geometries. These geometries are expected to be useful for the application of biometric authentication using finger blood vessels. For example, a cylindrical excitation/sensor array can surround the finger.

The invention claimed is:

1. Apparatus for thermoacoustic imaging, the apparatus comprising:
   a microwave source configured to provide a microwave output;
   a microwave emitter array including two or more unit cells, wherein the unit cells each comprise two or more near-field excitation elements;
   wherein the microwave emitter array is configured to receive the microwave output from the microwave source, and wherein the microwave emitter array is configured to provide microwave excitation to a target via the near-field excitation elements of the unit cells, wherein a spacing between the microwave emitter array and the target is 10 wavelengths or less, wherein the wavelength is a wavelength of the microwave emitter array within the target;
   wherein the microwave output is provided to the near-field excitation elements of the unit cells with relative phases selected to provide polarization eccentricity of 0.87 or less within the target;
   an acoustic sensor array having one or more sensor elements configured to receive acoustic signals from the target responsive to the microwave excitation;
   a processor configured to receive signals from the acoustic sensor array and to provide an acoustic image of the target.

2. The apparatus of claim 1, wherein the relative phases within each unit cell are substantially equally spaced apart.

3. The apparatus of claim 1, further comprising an optical source configured to provide optical radiation to the target.

4. The apparatus of claim 3, wherein the target comprises a first region closer to a surface of the target than a second region, wherein the optical radiation is mainly provided to the first region, wherein the microwave excitation is mainly provided to the second region, whereby depth uniformity of thermoacoustic imaging is improved.

5. The apparatus of claim 3, wherein the optical source is configured to provide optical radiation at two or more optical wavelengths, and wherein the optical radiation at the two or more optical wavelengths is configured to enhance depth uniformity of thermoacoustic imaging.

6. The apparatus of claim 3, wherein the microwave excitation and the optical radiation are provided synchronously using a single trigger signal.

7. The apparatus of claim 3 wherein the microwave excitation and the optical radiation are provided sequentially in alternation.

8. The apparatus of claim 3, further comprising one or more auxiliary sensors;
wherein the auxiliary sensors are selected from the group consisting of microwave sensors, optical sensors and acoustic sensors;
wherein the auxiliary sensors are configured to provide one or more functions selected from the group consisting of: monitoring and calibrating the microwave excitation, monitoring and calibrating the optical radiation, obtaining course-grain information about the target geometry and its motion, providing signals for cancellation of microwave to acoustic leakage directly with analog electronics, providing signals for cancellation of microwave to acoustic leakage computationally in post-processing, providing signals for cancellation of optical to acoustic leakage directly with analog electronics, providing signals for cancellation of optical to acoustic leakage computationally in post-processing.

9. The apparatus of claim 3, wherein optical emitters and the unit cells of the microwave emitter array alternate.

10. The apparatus of claim 1, wherein the microwave emitter array is periodic.

11. The apparatus of claim 1, wherein the microwave emitter array is aperiodic.

12. The apparatus of claim 1, wherein the microwave output comprises microwave signals at two or more frequencies.

13. The apparatus of claim 12, wherein the microwave signals at the two or more frequencies are configured to enhance depth uniformity of thermoacoustic imaging.

14. The apparatus of claim 1, wherein the acoustic sensor array and the microwave emitter array are disposed on the same side of the target.

15. The apparatus of claim 1, wherein the acoustic sensor array and the microwave emitter array are disposed on opposite sides of the target.

16. The apparatus of claim 1, wherein the microwave source is configured to provide microwave pulses having a duration of 1 µs or less, a peak power of 0.1 W or more, and a repetition rate of 1 Hz or more.

17. The apparatus of claim 1, wherein the microwave source is configured to provide a continuous amplitude-modulated microwave output.

18. The apparatus of claim 1, wherein non-adjacent unit cells are activated in sequence in order to reduce cross-talk between different unit cells.

19. The apparatus of claim 1, wherein non-adjacent sensor elements are activated in sequence in order to reduce cross-talk between different sensor elements.

20. The apparatus of claim 1, wherein the sensor array elements are individually tuned to different acoustic frequencies.

21. The apparatus of claim 1, wherein the apparatus is flexible in order to conform to a shape of the target.

22. The apparatus of claim 1, wherein the apparatus is rigid and has a non-planar geometry.

23. The apparatus of claim 1, wherein the apparatus is rigid and planar.

24. The apparatus of claim 1, wherein the microwave output is provided to the near-field excitation elements of the unit cells with relative phases selected to provide polarization eccentricity of 0.71 or less within the target.

25. The apparatus of claim 24, wherein the microwave output is provided to the near-field excitation elements of the unit cells with relative phases selected to provide polarization eccentricity of 0.32 or less within the target.

26. The apparatus of claim 8, wherein the auxiliary sensors are configured to provide signals for cancellation of microwave to acoustic leakage directly with analog electronics.

27. The apparatus of claim 8, wherein the auxiliary sensors are configured to provide signals for cancellation of microwave to acoustic leakage computationally in post-processing.

28. The apparatus of claim 8, wherein the auxiliary sensors are configured to provide signals for cancellation of optical to acoustic leakage directly with analog electronics.

29. The apparatus of claim 8, wherein the auxiliary sensors are configured to provide signals for cancellation of optical to acoustic leakage computationally in post-processing.

* * * * *